United States Patent [19]

Drew et al.

[11] Patent Number: 5,730,867

[45] Date of Patent: Mar. 24, 1998

[54] METHOD AND APPARATUS FOR LOW PRESSURE LIQUID CHROMATOGRAPHY

[76] Inventors: Keith Raymond Drew, Pennigton House, Pennington, Ulverston, Courbria LA127ny, United Kingdom; Nils Magnus Hjelm, Flat 9A, Block A, Prince of Wales Hospital, Shatik, N.T., Hong Kong

[21] Appl. No.: 729,033

[22] Filed: Oct. 9, 1996

Related U.S. Application Data

[63] Continuation-in-part of Ser. No. 448,974, May 24, 1995, abandoned, which is a continuation of Ser. No. 206,515, Jun. 14, 1988, abandoned.

[51] Int. Cl.$^6$ .................................................. B01D 15/08
[52] U.S. Cl. .................................. 210/198.2; 210/656
[58] Field of Search .................................. 210/635, 656, 210/101, 198.2, 232, 238; 422/70, 81, 80, 82; 436/66, 67, 161

[56] References Cited

U.S. PATENT DOCUMENTS

| | | | |
|---|---|---|---|
| Re. 29,454 | 10/1977 | Ashmead et al. | 210/198.2 |
| 4,116,046 | 9/1978 | Stein | 210/198.2 |
| 4,142,857 | 3/1979 | Acuff | 422/70 |
| 4,168,147 | 9/1979 | Acuff | 422/70 |
| 4,238,196 | 12/1980 | Acuff et al. | 210/198.2 |
| 4,243,534 | 1/1981 | Bulbenko | 210/656 |
| 4,270,921 | 6/1981 | Graas | 210/656 |

(List continued on next page.)

FOREIGN PATENT DOCUMENTS

| | | | |
|---|---|---|---|
| 1 167 278 | 5/1984 | Canada | 210/198.2 |
| 0 008 921 | 3/1980 | European Pat. Off. | 210/198.2 |
| 0 293 540 | 12/1988 | European Pat. Off. | 210/198.2 |
| 2 484 858 | 2/1982 | France | 210/198.2 |
| 60-159646 | 8/1985 | Japan | 210/198.2 |
| 60-183554 | 9/1985 | Japan | 210/198.2 |
| 63-75558 | 4/1988 | Japan | 210/198.2 |

OTHER PUBLICATIONS

Errser, "Packing Materials Suitable for Rapid Analytical, Low Pressure Chromatography of Haemoglobins on Midget Columns," pp. 183–188 Biomedical Chromatography, vol. 1, No. 41986.

Errser, "Automated, quantitative, low pressure, cation exchange Chromatography of Haemoglobins on Midget columns", pp. 92–96, Journal of Automatic Chemistry/Journal of Clinical Laboratory Automation vol. 9 No. 2, 1987.

*Primary Examiner*—Ernest G. Therkorn
*Attorney, Agent, or Firm*—Harness, Dickey & Pierce, P.L.C.

[57] ABSTRACT

A method and apparatus for low pressure liquid chromatography which is particularly suitable for the testing of body fluids and in particular blood, the method comprising the steps of passing a sample through a chromatography column containing a packing material so that a constituent of the sample is retained by the packing material and passing a buffer solution having a varying concentration through the column. When the concentration of the buffer solution reaches a particular level, the constituent will be disassociated from the packing material and flows out of the column through a detector. The detector measures the light absorption of the fluid and by relating the time varying light absorption of the fluid to the time varying concentration of the buffer solution, it is possible to identify the constituent. Samples of body fluid are conveniently taken by puncturing the skin and applying a capillary tube to the fluid which emerges. The capillary tube is then placed in a pre-filled sample vial containing a solution for processing the body fluid and, after a certain time, the vial is placed in the chromatography apparatus and is drawn into the apparatus for testing. The apparatus is controlled by a microprocessor operating according to a stored program, the chromatography column used is a two part plastic column about 5 mm long and adapted to operate at a pressure of about 15 psi. The two part nature of the column allows it to be filled particularly easily.

12 Claims, 4 Drawing Sheets

U.S. PATENT DOCUMENTS

| | | | |
|---|---|---|---|
| 4,288,322 | 9/1981 | Guillemin | 210/198.2 |
| 4,350,595 | 9/1982 | Gunkel | 210/198.2 |
| 4,409,335 | 10/1983 | Hanamoto et al. | 436/67 |
| 4,437,812 | 3/1984 | Abu-Shumays et al. | 210/198.2 |
| 4,451,365 | 5/1984 | Sattler et al. | 210/198.2 |
| 4,476,017 | 10/1984 | Scharff | 210/198.2 |
| 4,483,773 | 11/1984 | Yang | 210/198.2 |
| 4,517,241 | 5/1985 | Alpert | 428/332 |
| 4,595,495 | 6/1986 | Yotam et al. | 210/198.2 |
| 4,595,496 | 6/1986 | Carson | 210/198.2 |
| 4,636,315 | 1/1987 | Allen | 210/198.2 |
| 4,769,141 | 9/1988 | Couillard | 210/198.2 |
| 4,810,391 | 3/1989 | Bruegger | 210/656 |
| 4,879,039 | 11/1989 | Takahashi et al. | 210/635 |
| 4,902,414 | 2/1990 | James | 210/198.2 |
| 4,919,595 | 4/1990 | Likuski et al. | 417/18 |
| 5,089,124 | 2/1992 | Mahar et al. | 210/198.2 |

| PEAK | TYPE | RT(mins) | AREA | HEIGHT | BASE | |
|---|---|---|---|---|---|---|
| 1 | BB | 0.52 | 1.854 | 0.148 | -5.336 | 0.419 |
| 2 | BV | 4.60 | 62.649 | 1.774 | -5.281 | 14.166 |
| 3 | VB | 5.77 | 377.752 | 9.534 | -5.230 | 85.415 |

METHOD AND APPARATUS FOR LOW PRESSURE LIQUID CHROMATOGRAPHY

CROSS REFERENCE TO RELATED APPLICATIONS

This application is a continuation-in-part of U.S. application Ser. No. 08/448,974 filed May 24, 1995, which is a continuation of U.S. application Ser. No. 07/206,515 filed Jun. 14, 1988, both now abandoned.

FIELD OF THE INVENTION

The present invention relates to a method and apparatus for low pressure liquid chromatography and in particular to an automated, chromatography process designed to give quantitative results.

DESCRIPTION OF THE PRIOR ART

Liquid chromatography is a technique in which a sample containing constituents to be measured is passed into a chromatography column containing a packing material. The packing material is chosen so that the constituents which are to be measured associate with or bind to it in such a way that it can be disassociated by passing a certain concentration of a buffer solution through the column. Different substances will bind to the packing material with different strengths and so different concentrations of buffer will be needed to disassociate them from the packing material. The presence of the constituents in the solution passing out of the column is detected by measuring its light absorption at a certain wavelength. Thus, by knowing the concentration of the buffer which caused the constituent to disassociate from the packing material, the identity of the constituent is known. In the established techniques, the process is carried out at high pressure, i.e. several thousand psi, in steel chromatography columns about 30 cm long and 2 cm in diameter. Clearly, the construction of the column and associated apparatus needs to be sufficiently strong to withstand the high pressures used. The apparatus tends, therefore, to be bulky, heavy and expensive.

Liquid chromatography, in particular, cation-exchange chromatography can be used to analyze haemoglobins as it can detect the presence of different types of haemoglobins in the blood. For instance, haemoglobins with an abnormal amino acid sequence can be detected, such as haemoglobin S which results in sickle-cell anaemia or glycated haemoglobin (i.e. haemoglobin which has reacted with glucose) which is indicative of a previous high concentration of blood glucose resulting from a diabetic condition. The concentration of glycated haemoglobin is used to monitor the treatment of diabetes and is a better indicator of a patient's condition than the instantaneous blood glucose level which tends to vary quite considerably over the short-term—for instance, it rises quickly after a meal. The concentration of glycated haemoglobin varies on a longer time scale than the blood glucose level because blood bells are replaced about every 120 days, and so is representative of an average of the blood glucose level over the preceding few months. However, since liquid chromatography has required the use of the high-pressure complex equipment described above, even if alternative tests were used, it has been necessary for many clinics and smaller hospitals to send blood samples away for testing which usually takes several days and is, thus, unsatisfactory.

Recently, the development of new packing materials for chromatography columns have made it possible to use a small column of the order of 5 to 20 mm long and to perform the process at low pressure e.g. 10 to 30 psi. The samples are prepared manually and loaded manually on to the column, and then, one after the other, a number of different concentration buffers are individually passed through the column and the solution flowing out of the column monitored with the usual optical detector. Again, by knowing which buffer concentration caused which constituent to flow out of the column, the identity of the constituents is known. An example of this technique applied to blood testing is as follows. Blood collected into tubes containing EDTA anticoagulent is centrifuged and the plasma and white cells removed. The red cells (1 vol) are washed by mixing with isotonic saline (4 vol) and then centrifuged at 2000xg for 5 min. After repeating this washing process, the cells (1 vol) are haemolysed by vigorously mixing with 0.01M potassium cyanide solution (1.5 vol). They are then allowed to stand for 5 min to ensure all the haemoglobin were in the reduced form. Lipid material is removed by shaking with carbon tetrachloride (1 vol) for 30 s. After centrifuging, a portion of the clear supernatant (50 µL) is removed and mixed with the loading buffer (950 µL) appropriate to the analysis system under investigation. Portions of this solution (50 µL–1.5 µL of red cells) are loaded into the column. Various column packing materials can be used including CM cellulose, BioRex 70, Glycogel B and polyaspartic acid silicas. Columns of CM cellulose and polyaspartic acid silica are eluted with Bis-tris (bis(2-hydroxyethyl)imino-tris (hydroxymethyl)methane) buffer. Two stock buffers can be used: one, stock buffer (a) containing 40 mM Bis-tris and 4 mM potassium cyanide adjusted to pH 6.2 with concentrated hydrochloric acid, and a second stock buffer (b) comprising buffer (a) to which sodium chloride was added to a concentration of 200 mM before pH adjustment. These buffers can be mixed in various proportions to obtain eluents of intermediate sodium chloride concentration.

Columns of Biorex 70 are eluted with a modification of a known phosphate buffer system (e.g. described by Kynoch P.A.M. and Lehman H. (1977) Lancet ii, 16). Again, two buffers are used: buffer (a) was 41 mM sodium, pH 6.4, and extra sodium chloride was added to the original buffer (b) (136 mM sodium, pH 6.8) to a final concentration of 200 mM.

Columns of Glycogel B are equilibrated with ammonium acetate buffer (250 mM+50 mM MgSO$_4$, 3 mM NaN$_3$, pH 8.5) as described in, for example, Gould et al. (1982) Clin. Chim. Acta 125, 41.

All buffers were passed through a millipore filter (0.45 m) under reduced pressure before use. This process also helped to degas the solutions. The techniques are, however, still slow, and are too complex to be used by relatively unskilled technicians in individual clinics as the sample preparation requires several pieces of equipment and several preparation chemicals and the operation of the chromatography apparatus requires some skill.

OBJECTS OF THE INVENTION

It is an object of the invention to provide a simplified liquid chromatography process which is suitable for use by relatively unskilled technicians in individual clinics.

It is a further object of the invention to provide a liquid chromatography apparatus which is easy to use, provides easily understandable results and in which the parts which have a relatively short useful life are readily interchangeable and, when necessary, replaceable.

It is yet another object of the present invention to provide a liquid chromatography apparatus which includes an enhanced seal around the inlet and outlet apertures.

STATEMENT OF INVENTION

According to the present invention, there is provided a method of low pressure liquid chromatography comprising the steps of:

passing a sample to be tested by said chromatography method through a chromatography column containing a packing material in the column whereby a constituent of the sample is retained by the packing material; continuously and automatically controlling the concentration of a buffer solution as a predetermined continuous function of time for an interval of time to vary over that interval of time; and for said interval, automatically pumping the varying concentration buffer at a pressure substantially less than 100 psi through the column along the packing material whereby said constituent of the sample is freed from the packing material by a certain concentration of the buffer solution; and continuously measuring the concentration as a function of time of the said constituent in the solution flowing out of the column, wherein the chromatography column comprises a column body defining a chamber containing the column packing material, the body including means defining an inlet aperture and means defining an outlet aperture, said inlet and outlet aperture defining means also defining shoulders on the inside of the body and surrounding said apertures and on each of which is mounted a plastics disc for supporting the packing material, the body being in first and second parts so that the first part may be filled with the packing material before the two parts are connected together to form the column.

The present invention also provides apparatus for low pressure liquid chromatography comprising a chromatography column containing a packing material;

sample induction means for drawing a sample into the apparatus and passing it through the column whereby a constituent of the sample is retained in the packing material;

means for producing a buffer solution having a concentration which varies as a predetermined, continuous, function of time during an interval of time and for passing the varying concentration buffer solution through the column; and a detector for measuring the concentration of said constituent in the buffer solution flowing out of the column as a function of time.

Preferably, the apparatus further include display means for displaying the measured concentration as a function of time on a printed graph or a video display or both. Conveniently, the concentration of the buffer solution can be varied in the required manner, e.g., in a series of unidirectional steps (i.e., all increasing or all decreasing) by varying the mixing ratio of two solutions of different concentrations. This may be done by using a gradient valve connected to two reservoirs of the solutions combining the outputs of two syringes driven at separately controlled rates each containing a buffer solution having a different concentration. Preferably, the column is less than 10 mm long and uses polyaspartic acid-silica as a packing material. The process may be carried out between 10 and 30 psi and preferably at about 15 psi.

Preferably, the chromatography column is removably mounted in the apparatus conveniently by being squeezed between mountings including respectively an inlet and outlet for supplying fluid to and receiving fluid from the column. This allows the column to be easily removed and replaced.

Preferably, the apparatus and method are controlled by a microprocessor operating according to a stored program so that when the sample has been mounted in the apparatus it can simply be commanded to proceed and will then draw the sample into the apparatus, perform the analysis and display the results without any further action required by the operator.

The present invention also provides a method of testing blood constituents by using the method of low pressure liquid chromatography and apparatus described above. The sample may be prepared by placing a sample of blood onto a carrier, e.g. drawing it into a capillary tube, placing the carrier in a container of fluid which haemolises and dilutes the blood, and passing a sample of the resulting mixture into the column. Thus, the blood sample is easily taken by pricking the patient's finger and applying the capillary tube to the droplets of blood which emerges. The capillary tube itself is then dropped into a vial of the fluid, agitated for a certain time and then placed in the apparatus so that the fluid can be drawn into it. Preferably, the fluid used to treat the sample is one of the buffer solutions which is used in the chromatography process.

According to a further aspect, the present invention provides a chromatography column comprising a column body defining a chamber containing column packing material, the body including means defining an inlet aperture and means defining an outlet aperture, said means also defining shoulders on the inside of the body and surrounding said apertures and on each of which is mounted a plastic disc for supporting the packing material, the body being in first and second parts so that the first part may be filled with packing material before the two parts are connected together to form the column.

Preferably, the two parts of the body push-fit together in an interference fit so that they are held firmly together when mounted in the apparatus described above. Conveniently, the first part of the body is generally cylindrical and has a reduced diameter portion or an end wall at one end to define an aperture and an exterior diameter reduced portion at the other end over which one end of the second part fits. The other end of the second part also has an aperture in it, the two apertures forming the inlet and outlets for the column. Preferably, the parts of the column are made from an inert plastic material and may be made by injection molding of, for instance, a polycarbonate plastic.

The construction of the column as above allows it to be filled by a particularly simple procedure and according to a further aspect of the invention, there is provided a method of packing a chromatography column as described above comprising the steps of:

placing a first permeable plastic disc on the shoulders in the first part, placing a cylindrical collar over and extending from the diameter reduced portion;

filling the first part and at least partially filling the collar with a slurry containing a greater amount of packing material than is required to fill the column;

and applying a vacuum to the aperture in the first part to remove the fluid element of the slurry and pack the packing material onto the plastic disc;

removing the collar and slicing-off an excess of packing material;

placing a second permeable plastic disc on the shoulders in the second part and pressing the first and second parts together.

DESCRIPTION OF THE DRAWINGS

The invention will be further described by way of non-limitative example with reference to the accompanying drawings in which.

DESCRIPTION OF THE PREFERRED EMBODIMENT

Figure 1:
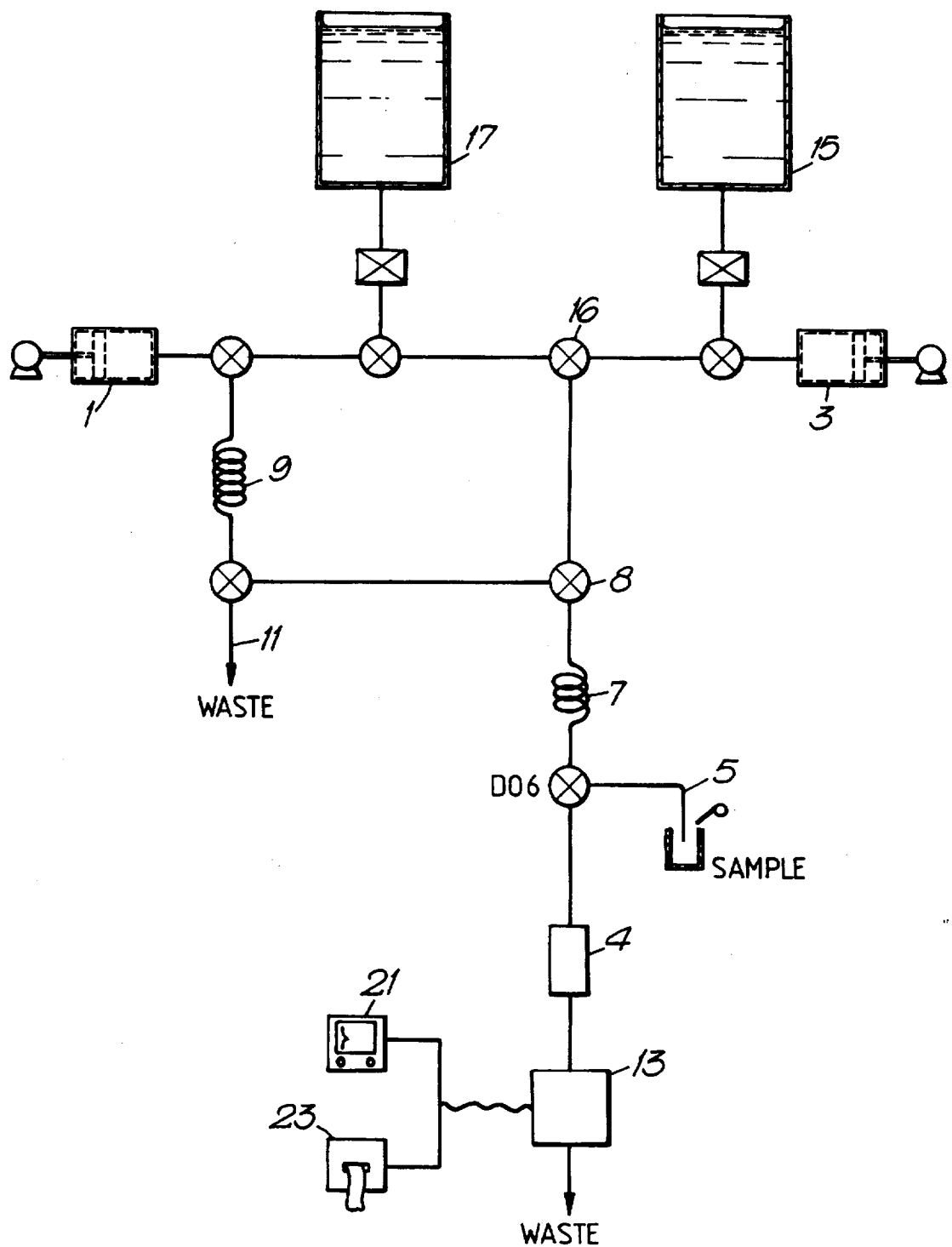
FIG. 1 is schematic diagram of the apparatus according to the present invention.

The chromatography apparatus of the present invention is shown schematically in FIG. 1. The main parts of the apparatus are two syringes 1 and 3 which are used to control the flow of fluids around the system, a chromatography column 4 attached to a detector 13, a sampling induction tube 5, two hold-up loops 7 and 9 which hold a fixed, predetermined volume of liquid and two reservoirs 15 and 17. The apparatus also includes a microprocessor which is used to control the syringes 1 and 3 via stepper motors and to control the various valves connecting the fluid parts together and to process and output the results from the detector 13.

The reservoirs for buffer solution can be either rigid plastic bottles or flexible aseptic containers similar to the well known wine boxes which have an outer box and inner collapsible bay.

Figure 4:
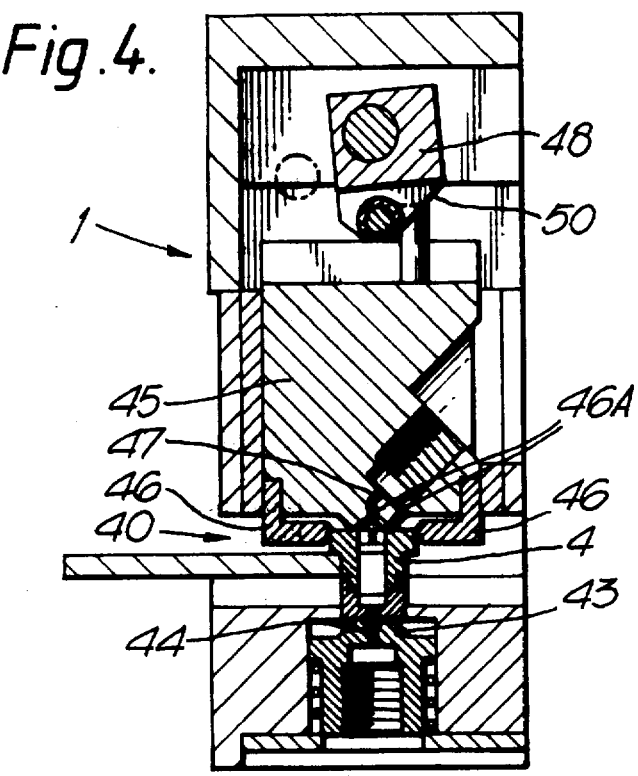
FIG. 4 is a side view of the column mounting in apparatus according to the present invention.
Figure 5:
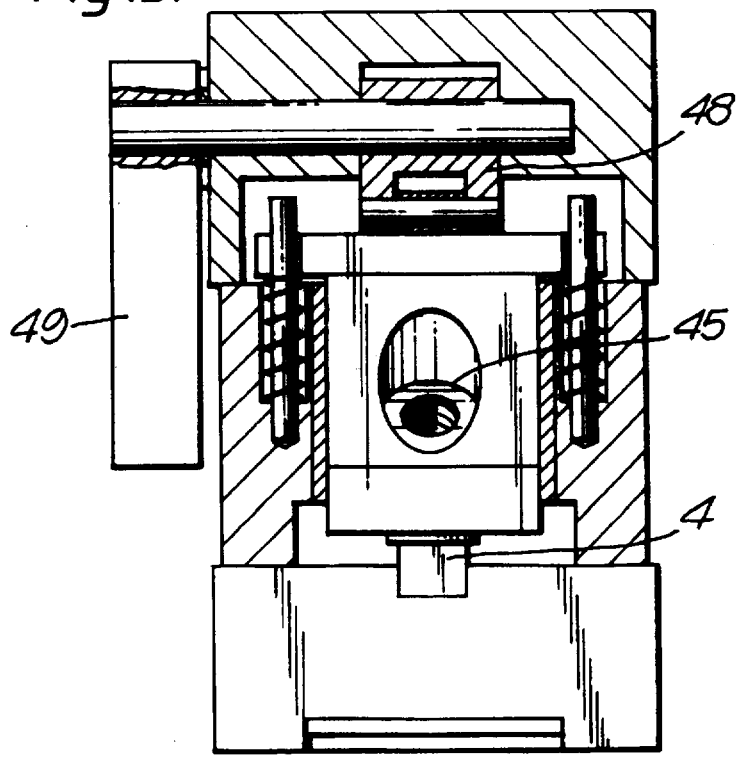
FIG. 5 is a back view of the column mounting shown in FIG. 4.

In use, the apparatus operates as follows. First, a sample is drawn up into the apparatus via the induction line 5. (This part of the apparatus is also shown in FIGS. 4 and 5). The sample is drawn up by syringe 1 via the two hold-up loops 7 and 9. Then valve 8 is closed to isolate the sample in hold-up loop 7 from the syringe while the sample in hold-up loop 9 is ejected as waste. This is done so that the sample in hold-up loop 7 which will actually be tested does not include the first fluid drawn from the sample which can be unsatisfactory for a number of reasons, e.g. because of contamination or air bubbles.

Subsequently, valve 8 is opened and syringe 1 pumps the sample onto the column 4. Various constituents of the sample will bind with different strengths to the packing material in the column.

The two buffer reservoirs 15 and 17 contain buffers of different concentrations and the two syringes 1 and 3 are filled respectively from the two reservoirs. Subsequently, under control of the microprocessor, the two syringes are driven so as to pump buffer solution to the mixing point 16 and from there through the column 4. The concentration of the mixed solution is clearly dependent on the respective rates of the two syringes and the concentrations of the buffers and so it is possible for the concentration of the mixed solution to be varied by the microprocessor according to a pre-stored program. Note that in the illustrated embodiment no mixing chamber is necessary, the solutions mix at the junction of the three tubes. A mixing chamber can be used if desired. Alternatively, a gradient valve connected directly to pressurized reservoirs, e.g. syringes driven at the same rate, can be used to control the concentration of solution supplied to the column. When the concentration of the buffer reaches a sufficient strength to disassociate a particular sample constituent from the column packing material, then that constituent will pass out of the column and through the detector 13 where it can be detected. The microprocessor is conveniently programmed to increase the concentration of buffer passing through the column gradually in a series of defined steps or in a continuous gradient. Thus, it will be known at any time exactly what concentration of buffer is passing through the column and, thus, which of these sample constituents is being disassociated from the column packing material and appearing in the detector. If this is done then by integrating the output of the detector, the amount of that constituent in the sample can be calculated and, thus, a quantitative result obtained.

Figure 6:
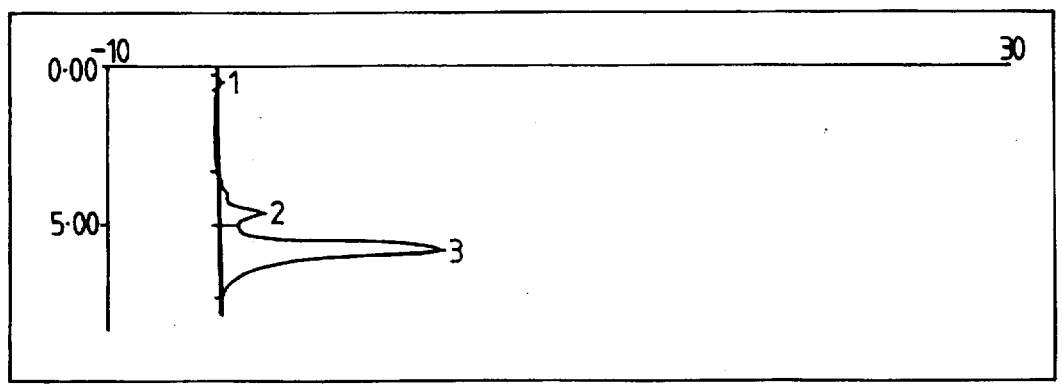
FIG. 6 shows the output results of using the apparatus according to the present invention.

The detector used is similar to that used in previous low pressure liquid chromatography apparatus and simply measures the light absorption at a certain wavelength of the fluid passing through it. The output is supplied to the microprocessor controlling the apparatus which also processes and outputs the results. The results are displayed in graphical form both as a hard copy via printer 23 and on a video display 21. An example of the results produced is shown in FIG. 6.

The control apparatus is designed so that when the apparatus is switched on, a number of blank runs are performed, e.g. five, that is runs without a sample on the column so that air bubles and contaminants are removed from the system. The system is preferably arranged to continue performing blank runs until the column is ready for use. The same procedure is also used when the machine is shut down. The circuitry also counts the number of times the column is used so that a limit can be set on the life of the column. In the present case the limit is approximately 100 samples as opposed to known HPLC columns which are typically used for anywhere from 1000 to 10000 assays requiring numerous washings during the life of the column.

Figure 3:
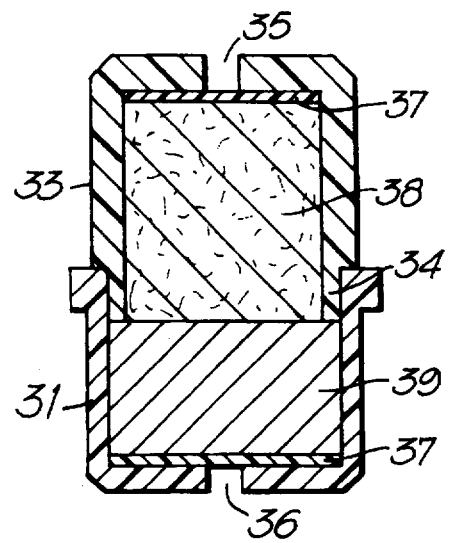
FIG. 3 shows a chromatography column according to the present invention.

The chromatography column of the present invention is shown in more detail in FIG. 3. It comprises a two-part plastic body consisting of a lower part 31 and an upper part 33. The two parts are formed so that they push-fit together in an interference fit by virtue of the wide, open-end of part 31 fitting around a portion 34 a reduced external diameter. An aperture 36 for fluid is provided in the end wall of the upper part 33 and a second aperture 35 is provided in the end wall of the lower part 31 (or along the shoulder 54 in lower part 31A). The apertures, otherwise referred to herein as inlets and outlets, are covered by permeable membranes 37 made from polyurethane or P.T.F.E. and the upper part 33 is filled with column packing material 38 by a process described below, the remainder of the volume in the column being made up by inert permeable material 39.

Figure 7:
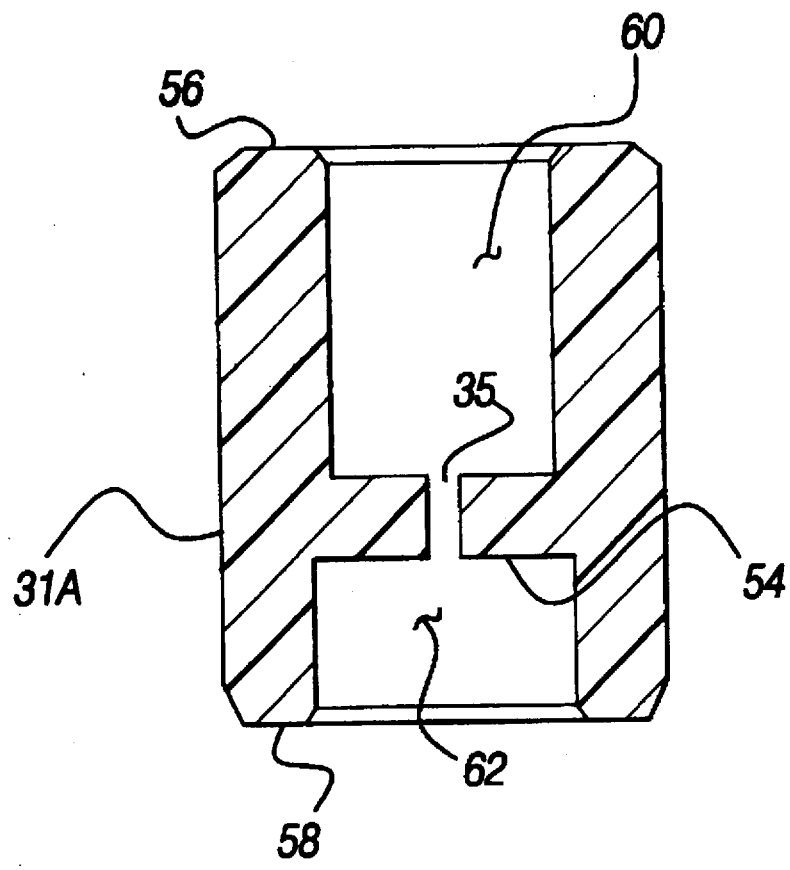
FIG. 7 shows an alternative lower portion for the column structure of the present invention.

Additionally, referring to FIG. 7, an alternative lower part 31A useful in association with the upper part 33 as described with reference to FIG. 3 is illustrated. Under this alternative embodiment, the lower part 31A includes a shoulder 54 extending into a first chamber 60 wherein the shoulder is spaced between the upper and lower ends 56 and 58, respectively, of the lower portion 31A. This arrangement provides for a second chamber 62 occurring below the shoulder 54 onto which one end of the mounting can extend to provide both a fluid tight seal along the aperture 35 and a more thoroughly packed column.

The construction of the column allows a particularly simple method to be used for packing it. This method is relatively quick and suitable for automation and gives reliably packed columns. First, the polyurethane filter is placed in an inverted upper part 33 and an open ended cylinder or collar is fitted over and extends from the diameter reduced portion 34. Then, the column part 33 and collar are filled with a slurry containing a greater amount of packing material 38 than is required to fill the column and a vacuum applied to aperture 36. This draws off the fluid and leaves the column packing material packed in the column part 33 and the collar. The collar is then twisted and removed leaving the column packing material standing proud of the end of the column part 33, and an excess of packing material is sliced off. The lower part 31 (or 31A depending on which is being used) with its polyurethane filter 37 already in place and filled with inert porous material is fitted onto the upper part 33 to complete the column. The slicing of the excess packing material can be performed using a rotating cutter to leave a hump in the middle so that when the two parts of the column are pushed together the packing material is placed under compression. In an embodiment of the invention which is particularly suited for testing haemoglobins in blood, the column packing material used is polyaspartic acid bonded to silica beads.

The completed column is fairly resistant to rough handling, particularly compared to prior art columns, and so used columns can be handled and replaced by relatively unskilled technicians, and replacement columns can be despatched to clinics by mail etc. Furthermore, the columns can be produced relatively cheaply.

The part of the chromatography apparatus which holds the column is shown in FIGS. 4 and 5. It comprises a lower mounting 43 which includes a fluid path 44 through which fluid is supplied to the column and an upper mounting 45 including a fluid path 47. The upper mounting includes an outer seat 46 which abuts the top corners of the column and an inner seat 46A which abuts and seals to the end of the column and surrounds the outlet from the column. Fluid from the outlet of the column passes through the region within the inner seat 46A and via an outlet 47 to the main part of the apparatus. The upper mounting 45 is moveable between the illustrated lower position and an upper position in which the seats 46 and 46A are raised above the column so that the column can be lifted out of the apparatus through the opening 40 in the front. The mounting is moved by a cam arrangement 48 operated by handles 49 (see FIG. 5) and the operating surface 50 of the cam arrangement is configured so that the mounting will remain stationary in either of its positions.

It will be recalled that the illustrated column is formed of two parts which push together, and it will, therefore, be appreciated that the pressure exerted on the column by the upper mounting when it is lowered tends to hold the column together. FIG. 5 shows a rear view of the mounting part of the apparatus and more clearly shows the handles 49 of the cam arrangement.

Figure 2:
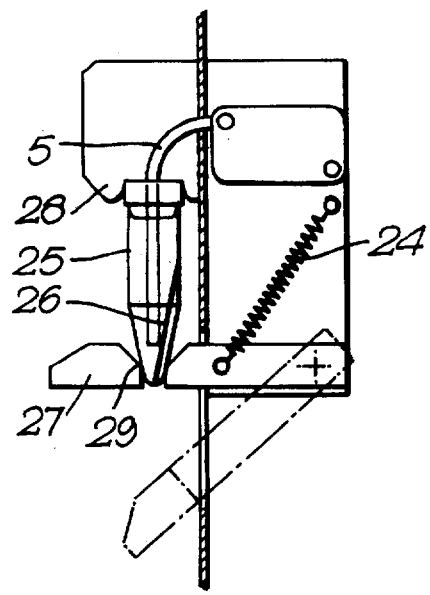
FIG. 2 shows the sample loading part of the apparatus according to the present invention.

The sample induction part of the apparatus is shown in detail in FIG. 2. It is designed to take a sample from a standard medical vial 25. The induction part includes a moveable lower platform 27 which is moveable between a raised position shown in full and a lowered position shown dotted and is urged towards its upper position by a spring 24. It also includes an upper seat 28 through which the sample induction tube 5 extends. The vial is placed over the induction tube 5 with its upper edge near the seat 28 while the platform is held in its lowered position. The moveable platform 27 is allowed to rise to its upper position to support the lower part of the vial and hold the vial in position with its open end against the seat 28. In the present embodiment, which is intended to be used with a method of collecting the samples which will be described below, the sample vial 25 will contain a capillary tube 26 (originally used to collect the sample). While the illustration shows the platform arranged to hold the vial vertically, in an alternative embodiment in order that this capillary tube does not impede the sample induction tube 5, the platform is arranged so as to tilt the sample vial so that the capillary tube falls to one side and clears the sample inlet tube 5.

The present invention is particularly intended for use in analyzing blood samples and is designed to be suitable for use by operators with relatively little training. One of the main problems with prior art techniques as mentioned above, is the skill required to take a blood sample and prepare it so that it is suitable for analysis. The present invention, however, is designed to work with the blood sample taken in a particularly simple way and processed in a single solution process.

According to the present invention, a blood sample is taken not by a syringe, but instead simply by pricking the patient's finger and applying a capillary tube to the droplet of blood which emerges. The capillary tube in this embodiment has a volume of 20 microliters. The capillary tube is then placed in a standard sample vial containing a solution which dilutes and haemolises the blood. In this embodiment, the sample vials are pre-filled with 1 mL of the processing solution. Different amounts can be used. No filtration or centrifuging of the resultant mixture is necessary; the sample is simply agitated, e.g. shaken by hand, for a recommended time, e.g. not less than five minutes, and then placed in the sample induction part of the apparatus as described above.

In an embodiment of the invention which is intended for testing the haemoglobins in blood samples, and particularly to test for glycated haemoglobins, the processing solution is one of the buffer solutions used in the elution process, in this case buffer A described below, and the vial needs to be agitated for not less than five minutes before being placed in the apparatus.

The testing apparatus is programmed with a number of tests which it can carry out automatically on command of the operator. Thus, it will be possible for a number of tests to be available, each selected by only one or two button operation. After the type of test has been entered and a "start" switch operated, the machine automatically executes the induction of the sample, testing and processing the results and displays the output in the required form.

FIG. 6 shows a typical output of a blood analysis for glycated haemoglobin. This was carried out using the apparatus described earlier and using the following two buffer solutions:

Buffer A
  Bis-Tris 40 mM:—41.84 g/5 L
  KCN 4 mM:—1.30 g/5 L
  NaN$_3$ (azide) 3 mM:—1.00 g/5 L
Buffer B
  NaCl 200 mM:—58.44 g/5 L
  Bis-Tris 40 mm:—41.84 g/5 L
  KCN 4 mM:—1.30 g/5 L
  NaN3(azide) 3 mM:—1.00 g/5 L The first large peak, labelled 2, is glycated haemoglobins passing through the detector and the second peak 3 represents non-glycated haemoglobins passing through the detector. As can be seen from the table below the graph, the processing circuitry automatically works out the area of beneath of the peaks (allowing for their overlap), i.e. integrates the curve, and this represents the total amount of glycated haemoglobins in the sample. The processing circuitry in this embodiment is also programmed in this to look out for certain other peaks in the sample which might be representative of other haemoglobin abnormalities.

The detector 13 can be provided with means for measuring at several different wavelengths, e.g. by using a tunable laser or by having several different fixed frequency light sources in it, or an achromatic light source with a number of interchangeable filters. Thus, tests at several different wavelengths are available. Thus, by using different buffer solutions and (if necessary) different column packing materials (easily used by virtue of the easily replaceable column) the apparatus can provide a wide variety of tests all of which are relatively simple for the operator to select.

The syringes, column, fluid paths detector and displays and the electronic processing circuitry all form a single unit of such a size that it can be conveniently mounted on a desk top. The apparatus is, therefore, very suitable to use in individual clinics. A clinic would be provided with a supply of suitable buffer solutions, pre-filled sample vials and capillary tubes of the correct length for taking samples and a number of replacement columns. The supply of buffer solutions and column vials and capillary tubes could be replenished on demand or at regular intervals and all of the equipment is tough enough to withstand rough handling and are light and small enough so they can be despatched by mail etc. This means that individual clinics can make tests, e.g. blood tests, instantly on their own premises and thus have a blood test result within minutes of a sample being taken. Further, the staff do not need specialist training in order to use the apparatus or replace the column etc. The equipment supplied to a clinic and the set of replacement materials can also include a standard sample (in a marked vial) which can be passed through the apparatus for quality control purposes. It would also be possible to run a blind quality control system in which samples whose composition is known only to the quality inspector are despatched to the clinics and the results returned to the inspector.

The present invention, therefore, provides a relatively small circuit which is easy to use and could be used on an individual basis by clinics, hospitals and surgeries around the world. Further, all of the parts which are used up during testing can be replenished easily, e.g. by dispatching a pack of columns, buffer solutions, pre-filled vials and capillary tubes to the user. The apparatus is also suitable for programming and performing a wide variety of tests for haemoglobin abnormalities.

The volume of the capillary tube is 20 micro liters and the vials are pre-filled with the solution required to process the sample.

The above description is given by way of example and numerous modifications and variations will be apparent to those skilled in the art without departing from the spirit and scope of the invention which is defined by the claims appended hereto.

We claim:

1. Apparatus for low pressure liquid chromatography comprising:

a chromatography column containing a packing material and comprising a column body defining a chamber containing the column packing material, the body including a first body part including means defining an inlet aperture and a second body part including means defining an outlet aperture, said inlet and outlet aperture defining means each also defining shoulders facing into said chamber and surrounding said apertures and on each of which is mounted a plastic disc for supporting the packing material;

the apparatus having first and second mountings, said first mounting including means defining an inlet port and said second mounting including means defining an outlet port for supplying fluid to and receiving fluid from the column;

at least one of the mountings being movable between a first position in which the column may be inserted between the mountings and a second position in which the column is retained between the mountings with said first and second body parts being urged together by said mountings and with said inlet and outlet ports respectively sealed to said inlet and outlet apertures;

sample induction means for drawing a sample into the apparatus and passing it through the column whereby a constituent of the sample is retained in the packing material;

means for producing a buffer solution having a concentration which varies as a predetermined continuous function of time during an interval of time and for passing the varying concentration buffer solution through the column; and a detector for measuring the concentration of said constituent in the fluid flowing out of the column as a function of time.

2. Apparatus according to claim 1, further comprising display means for displaying the measured concentration as a function of time on at least one of a printed graph and a video display.

3. Apparatus according to claim 1, wherein column packing material is polyaspartic acid-silica.

4. Apparatus according to claim 1, wherein said column is less than 100 mm long.

5. Apparatus according to claim 4, wherein said column is 5 mm long.

6. Apparatus according to claim 1, further comprising a holder for receiving a container containing the sample; and wherein said sample induction means are adapted to draw the sample from the container when it is in position on the holder.

7. Apparatus according to claim 1, wherein said means for producing the buffer solution comprises mixing means for mixing two solutions of different concentrations at a mixing ratio which is a controlled function of time.

8. Apparatus according to claim 7, wherein the mixing means comprises two syringes connected to a common outlet and including means for driving the syringes at independently controllable rates.

9. Apparatus according to claim 7, wherein said mixing means comprises a gradient valve.

10. Apparatus according to claim 7, including a mounting for receiving two reservoirs for said two buffer solutions.

11. Apparatus according to claim 10, wherein the mounting is a mounting for a flexible plastic bag of fluid.

12. Apparatus according to claim 1, including a microprocessor for controlling the sample induction means, buffer solution producing means and the detector according to a stored program and for monitoring the output of the detector and processing it according to a controlled program.

* * * * *

UNITED STATES PATENT AND TRADEMARK OFFICE
CERTIFICATE OF CORRECTION

PATENT NO. : 5,730,867
DATED : March 24, 1998
INVENTOR(S) : Drew, et al

It is certified that error appears in the above-identified patent and that said Letters Patent is hereby corrected as shown below:

Column 6, line 27, "bubles" should be --bubbles--.

Column 8, line 57, "40mm" should be --40 mM--.

Column 8, line 60, "NaN3" should be --NaN$_3$--.

Signed and Sealed this

Fourteenth Day of July, 1998

Attest:

Attesting Officer

BRUCE LEHMAN

Commissioner of Patents and Trademarks